US00PP14334P39

(12) United States Plant Patent
Zary

(10) Patent No.: US PP14,334 P3
(45) Date of Patent: Dec. 2, 2003

(54) SHRUB ROSE PLANT NAMED JACAPSHR

(50) Latin Name: *Rosa hybrida*
Varietal Denomination: JACenram

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/126,198

(22) Filed: Apr. 19, 2002

(65) Prior Publication Data

US 2003/0200583 P1 Oct. 23, 2003

(51) Int. Cl.[7] ..... A01H 5/00

(52) U.S. Cl. ..... Plt./102

(58) Field of Search ..... Plt./102

*Primary Examiner*—Bruce R. Campell

*Assistant Examiner*—Annette H. Para

(74) *Attorney, Agent, or Firm*—Klarquist Sparkman, LLP

(57) ABSTRACT

Shrub rose plant having high petal count; lack of anthers; strong spicy fragrance; disease resistant foliage; ability to propagate and grow on its own roots; and apricot flowers presented in large clusters.

1 Drawing Sheet

Botanical classification: *Rosa hybrida.*

SUMMARY OF THE INVENTION

The present invention relates to a new and distinct variety of rose plant of the shrub class which was originated by me by crossing an unnamed seedling with the variety JACenram (U.S. Plant Patent application pending).

BACKGROUND OF THE INVENTION

The primary objective of this breeding was to produce a new rose variety having the compact shrub habit, fragrance and disease resistance of the male parent combined with the high petal count and glassy foliage of the unnamed yellow seedling.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. High petal count;
2. Lack of anthers;
3. Strong, spicy fragrance;
4. Disease resistant foliage;
5. Ability to propagate and grow on its own roots; and
6. Apricot flower spresented in large clusters.

Asexual reproduction of this new variety by rooting cuttings, as performed at Somis, Calif. and Wasco, Calif., shows that the foregoing and all other characteristics and distinctions come true to form and are established and transmitted through succeeding propagations.

COMPARISON WITH PARENTS

Unnamed seedling female has bright yellow, small, two inch flowers and small glossy foliage. The male parent is a lavender pink compact shrub rose. JACapshr has apricot three inch flowers on a compact shrub.

COMPARISON WITH SIMILAR VARIETY

JACapshr is unique in flower color, plant habit and fragrance. Closest to it is the variety JACsuyel (unpatented) which is a yellow shrub rose with a different flower color and fewer petals. The plant habits are similar but JACapshr is more compact.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unpatented).

*Pollen parent.*—JACenram (U.S. Plant Pat. No. 12,995).

Classification:

*Botanical.*—*Rosa hybrida.*

*Commercial.*—Shrub.

FLOWER

Observations made from plants of one year of age grown in a garden environment at Somis, Calif., January–November 2001.

Blooming habit: Continuous.

Bud:

*Size.*—About 12–14 mm long when the petals start to unfurl.

*Form.*—The bud form is short, globular.

*Color.*—When sepals first divide, bud color is principally Red Group 37C with some petals occassionally being Red Group 41B in center. When half blown, the upper sides of the petals are Orange Group 29C; and the lower sides of the petals are Orange Group 29D.

*Sepals.*—Color: Upper surface: Green Group 137B; Lower surface: Yellow-Green Group 146C. Length: 24–30 mm. Width: 5–7 mm. Shape: Subulate. Surface texture: Upper: Hoary. Lower: Glandular. There are three heavily appendaged sepals. There are two unappendaged sepals with hairy edges.

*Receptacle.*—Color: Yellow-Green Group 146C. Shape: Pear. Size: Medium, about 6–8 mm long×5–7 mm wide. Surface: Smooth with a few glands.

*Peduncle.*—Length: Medium, averaging about 10–20 cm. Surface: Glandular. Color: Yellow-Green Group 146D with Greyed-Purple Group 184B blush. Strength: Erect.

Bloom:

*Size.*—Small. Average open size is 5–6 cm.

*Borne.*—In pyramidal clusters of 10–15 blooms.

*Stems.*—Strength: Normal. Average length is about 20–30 cm.

*Form.*—When first open: Bloom is globular. Permanence: Retains its form to the end.

*Petalage.*—Number of petals under normal conditions: 50–60.

*Color.*—The upper sides of the petals are Orange Group 29C. The reverse sides of the petals are Orange Group 29D. The base of each petal is Yellow-Orange Group 15C. The major color on the upper side is Orange Group 29C.

*Variegations.*—None.

*Discoloration.*—The general tonality at the end of the first day: Orange Group 29C. At the end of the third day: Orange Group 27B. At the end of the seventh day: Fades to Orange Group 27D at petal drop.

*Fragrance.*—Strong, spicy.

Petals:

*Texture.*—Thin.

*Shape.*—Spatulate.

*Margin.*—Entire.

*Apex shape.*—Obtuse/truncate.

*Base shape.*—Attenuate.

*Form.*—Tips slightly recurved.

*Arrangement.*—Imbricated. Petaloids in the center are few, small. Petaloid Color: Orange Red Group 33C.

*Persistence.*—Petals drop off cleanly before drying.

*Lastingness.*—On the plant: Long (about 7–9 days). As a cut flower: Long (about 9–11 days).

Reproductive parts:

*Stamens.*—None.

*Pistils.*—Number: 50–60. Styles: Color: Greyed-Yellow Group 160D. Length: 4–8 mm. Stigmas: Color: Greyed-Yellow Group 162B.

*Hips.*—None observed.

Plant:

*Form.*—Shrub.

*Growth.*—Very vigorous, upright, branching, compact. At maturity, height is 70–80 cm, width is 55–65 mm.

Foliage: Number of leaflets on normal mid-stem leaves: 5–7.

*Size.*—Medium (80 cm long×55 cm wide).

*Quantity.*—Normal.

*Color.*—New foliage: Upper side: Green Group 139A. Lower side: Green Group 137B. Old foliage: Upper side: Green Group 137A. Lower side: Yellow-Green Group 146B.

Leaflets:

*Size.*—Length: 30–35 mm. Width: 15–20 mm.

*Shape.*—Ovate.

*Tip shape.*—Rounded.

*Apex shape.*—Acuminate.

*Texture.*—Upper side: Glossy.

*Edge.*—Serrated.

*Serrations.*—Single, small.

*Petiole color.*—Yellow-Green Group 146C.

*Petiole rachis.*—Color: Lower side: Yellow-Green Group 146C. Upper side: Greyed-Orange Group 176C.

*Auricle shape.*—Not present.

*Stipules.*—Medium (about 16–18 mm glandular.)

*Disease resistance.*—Resistant to mildew, blackspot and rust under normal growing conditions.

Wood:

*New wood.*—Color: Yellow-Green Group 146D with Greyed-Red. Group 181B blush. Bark: Smooth.

*Old wood.*—Color: Yellow-Green Group 146B. Bark: Smooth.

Prickles:

*Quantity.*—On main canes from base: None. On laterals from main canes: Ordinary.

*Form.*—Hooked downward. Length: 5–7 mm.

*Color when young.*—Red Group 53B.

*Color when mature.*—Greyed-Orange Group 177C.

Small prickles:

*Quantity.*—On main stalks: None. On laterals: None.

Winter hardiness: Hardy to Zone 5.

I claim:

1. A new and distinct variety of rose plant of the shrub class, substantially as herein shown and described, characterized particularly by high petal count; lack of anthers; strong spicy fragrance; disease resistant foliage; ability to propagate and grow on its own roots; and apricot flowers presented in large clusters.

* * * * *

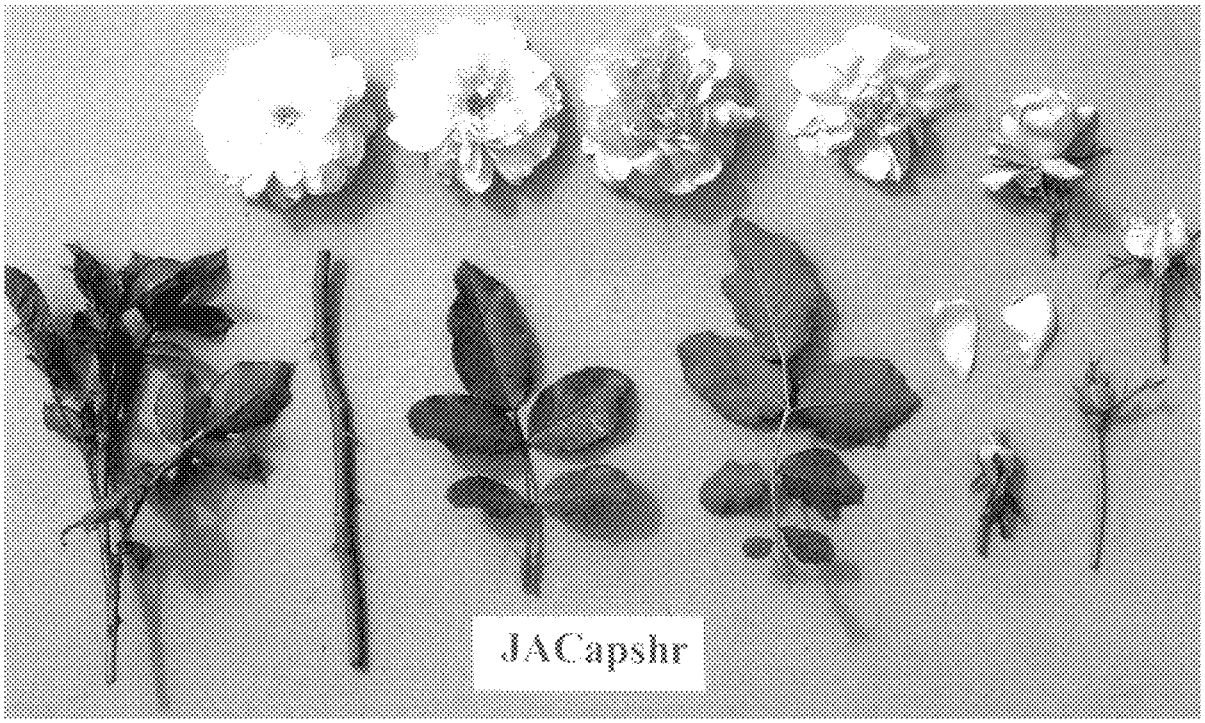
JACapshr